US005785655A

United States Patent [19]

Goodsell, Jr. et al.

[11] Patent Number: 5,785,655

[45] Date of Patent: Jul. 28, 1998

[54] TWO-DIMENSIONAL ULTRASOUND DISPLAY SYSTEM

[75] Inventors: Leonard James Goodsell, Jr., Palo Alto; Janice L. Marshall, Sunnyvale; Ismayil M. Guracar, Redwood City; Matthew I. Haller, San Francisco; Christopher R. Cole, Cupertino, all of Calif.

[73] Assignee: Acuson Corporation, Mountain View, Calif.

[21] Appl. No.: 822,064

[22] Filed: Mar. 24, 1997

Related U.S. Application Data

[62] Division of Ser. No. 620,283, Mar. 22, 1996, Pat. No. 5,724,974.

[51] Int. Cl.$^6$ .......... A61B 8/06

[52] U.S. Cl. .......... 600/441; 600/455

[58] Field of Search .......... 128/661.04–661.05, 128/661.08–661.1; 600/440–441, 451–456

[56] References Cited

U.S. PATENT DOCUMENTS 4,067,236 1/1978 Hottinger .
4,103,679 8/1978 Aronson .
4,265,126 5/1981 Papadofrangakis et al. .
4,373,533 2/1983 Iinuma .
4,476,874 10/1984 Taenzer et al. .
4,501,277 2/1985 Hongo .......... 128/660.05
4,509,526 4/1985 Barnes et al. .
4,790,322 12/1988 Iinuma .
4,800,891 1/1989 Kim .
4,873,985 10/1989 Nakajima .
4,928,698 5/1990 Bonnefous .
5,010,528 4/1991 Ohtsuki et al. .
5,014,710 5/1991 Maslak et al. .
5,062,427 11/1991 Seo et al. .
5,195,521 3/1993 Melton, Jr. et al. .
5,197,477 3/1993 Peterson et al. .......... 128/660.05 X
5,280,787 1/1994 Wilson et al. .
5,322,067 6/1994 Prater et al. .
5,419,332 5/1995 Sabbah et al. .......... 128/661.09
5,425,365 6/1995 Iinuma .......... 128/661.09
5,453,575 9/1995 O'Donnell et al. .
5,471,990 12/1995 Thirsk .
5,476,097 12/1995 Robinson .
5,479,926 1/1996 Ustunner et al. .
5,505,204 4/1996 Picot et al. .
5,515,857 5/1996 Tsujino et al. .......... 128/661.1
5,553,620 9/1996 Snider et al. .......... 600/440
5,568,812 10/1996 Murashita et al. .......... 128/660.04
5,622,174 4/1997 Yamazaki .......... 128/661.09
5,690,111 11/1997 Tsujino .......... 600/440

OTHER PUBLICATIONS

"Angle Independent Doppler Color Imaging: Determination of Accuracy and a Method of Display", Ding–Yu Fei et al., *Ultrasound in Med. & Bio.*, vol. 20, No. 2, 1994, pp. 147–155.

"Quantitative Measurement of Volume Flow Rate (Cardiac Output) by the Multibeam Doppler Method", H. Tsujino et al., *Journal of the American Society of Echocardiography*, Sep.–Oct. 1995, pp. 621–630.

"How to Measure Cardiac Output Accurately Within Just Seconds", product brochure published by Toshiba Medical Systems Europe.

(List continued on next page.)

*Primary Examiner*—Francis Jaworski
*Attorney, Agent, or Firm*—Brinks Hofer Gilson & Lione

[57] ABSTRACT

A user defines a line of study by two or more icons placed on a two-dimensional motion image. A velocity profile or the estimated spectra at each point along the line of study are displayed as a function of position along the line of study. The velocity and variance parameters displayed are computed in reference to velocity direction angles selected by the user. The information displayed is obtained from scan converted information to facilitate the process. One or more spectral strips may be displayed in addition at one or more range gate positions.

72 Claims, 7 Drawing Sheets

OTHER PUBLICATIONS

"Ultrasound Diagnostic Powervision SSA-380A" Toshiba Systems Data No. MSDUS0007EA. Toshiba Corporation. pp. 1-15, 1994.

CVI/CVI-Q Primer Informational booklette on the P700 SE System by Philips (publication date not available).

"Fractional Moving Blood Volume: Estimation with Power Doppler US[1]", Jonathan M. Rubin, MD, PhD, et al., *Radiology*, vol. 197, No. 1, Oct. 1995, pp. 183-190.

Toshiba Corporation Brochure entitled: Sonolayer Phased Array Scanner with Color Flow Imaging Model SSA-270A. Date Unknolwn. Total 12 Pages.

Toshiba Corporation Brochure entitled: "Sonolayer Phased Array Sector Scanner With Color Flow Imaging Model SSH-160A." Date Unknown. Total 24 Pages.

FIG. 1B
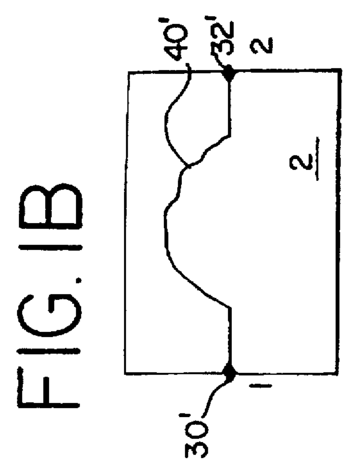
FIG. 1C
FLOW= 2.4 ml/s
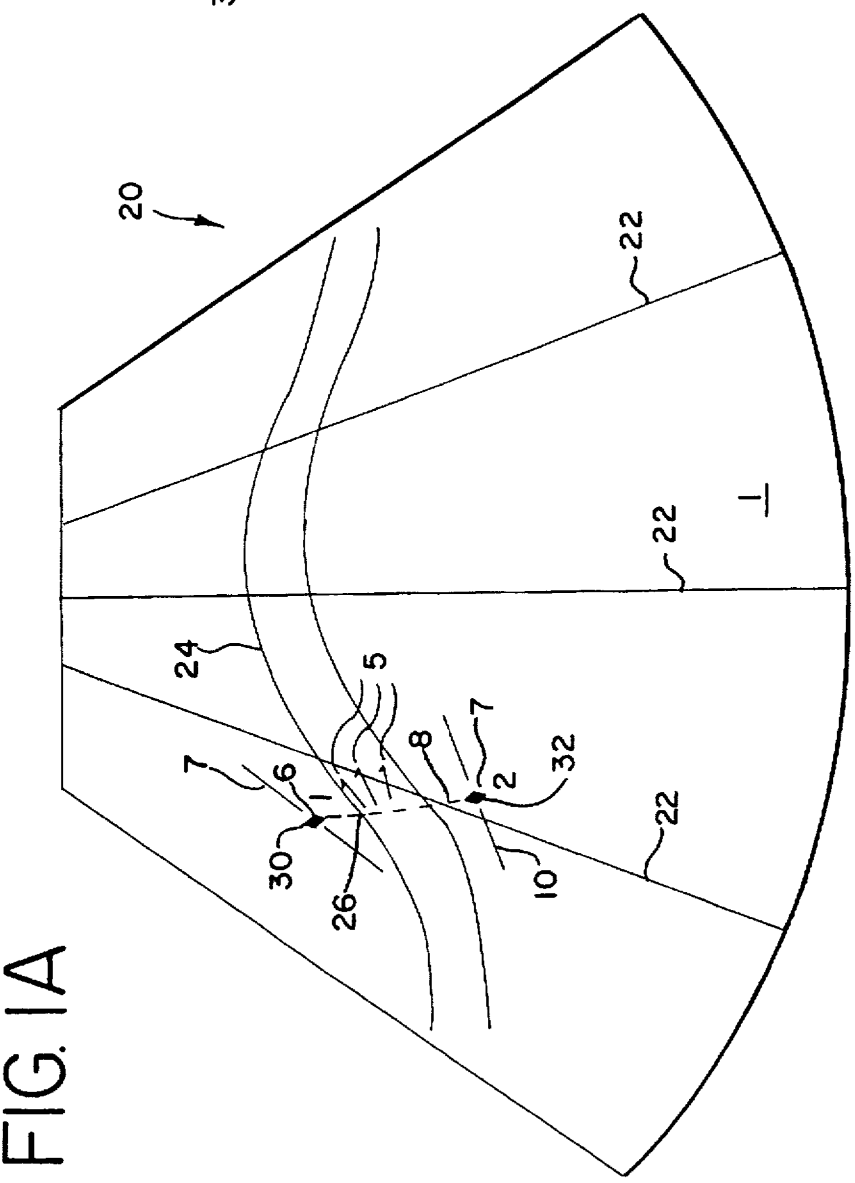
FIG. 1A

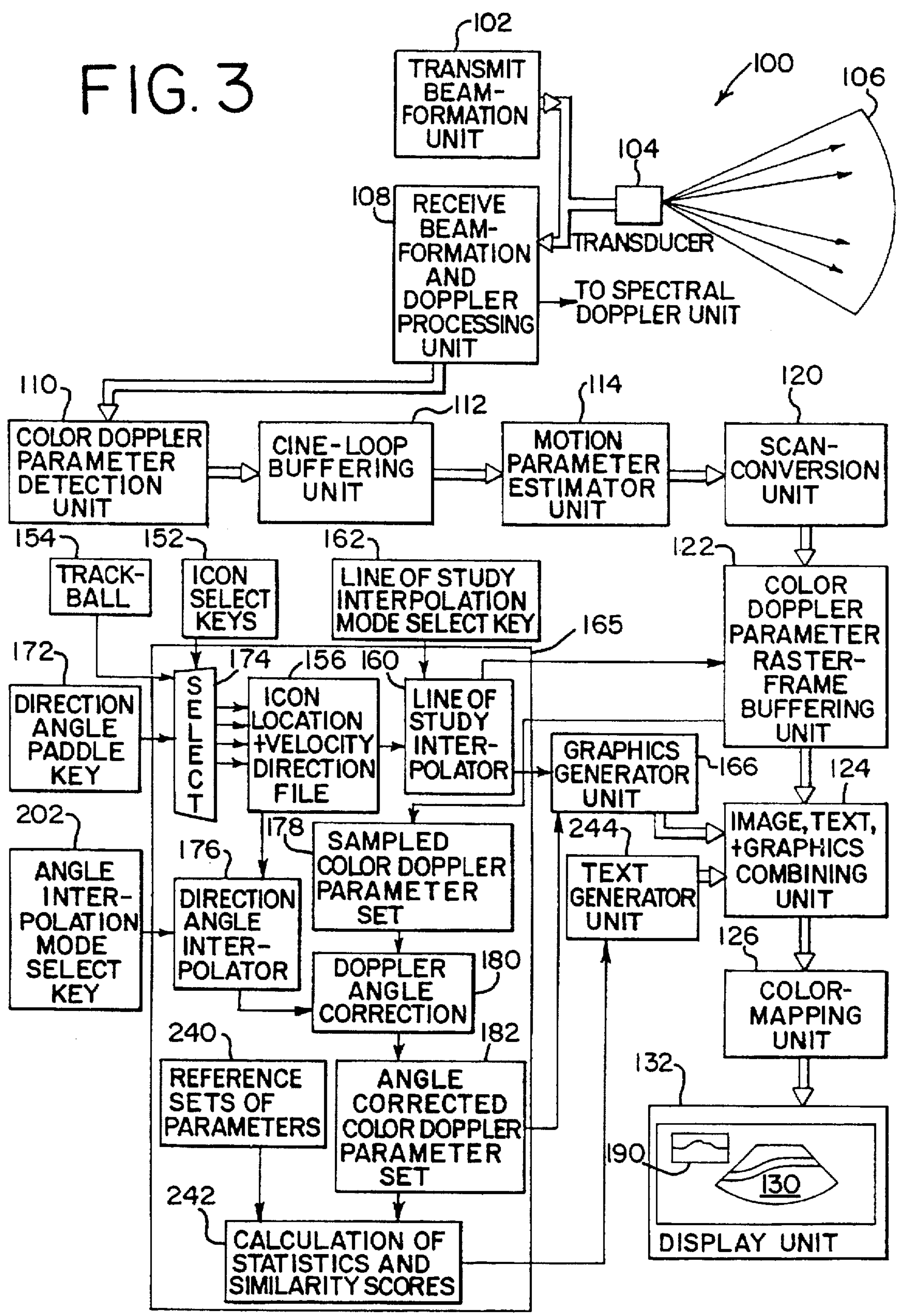
FIG. 3
TRANSMIT BEAM-FORMATION UNIT
102
100
106
104
TRANSDUCER
108
RECEIVE BEAM-FORMATION AND DOPPLER PROCESSING UNIT
TO SPECTRAL DOPPLER UNIT
110
COLOR DOPPLER PARAMETER DETECTION UNIT
112
CINE-LOOP BUFFERING UNIT
114
MOTION PARAMETER ESTIMATOR UNIT
120
SCAN-CONVERSION UNIT
154
TRACK-BALL
152
ICON SELECT KEYS
162
LINE OF STUDY INTERPOLATION MODE SELECT KEY
165
122
COLOR DOPPLER PARAMETER RASTER-FRAME BUFFERING UNIT
172
DIRECTION ANGLE PADDLE KEY
174
SELECT
156
ICON LOCATION +VELOCITY DIRECTION FILE
160
LINE OF STUDY INTER-POLATOR
GRAPHICS GENERATOR UNIT
166
124
IMAGE, TEXT, +GRAPHICS COMBINING UNIT
202
ANGLE INTER-POLATION MODE SELECT KEY
176
DIRECTION ANGLE INTER-POLATOR
178
SAMPLED COLOR DOPPLER PARAMETER SET
244
TEXT GENERATOR UNIT
126
COLOR-MAPPING UNIT
DOPPLER ANGLE CORRECTION
180
240
REFERENCE SETS OF PARAMETERS
182
ANGLE CORRECTED COLOR DOPPLER PARAMETER SET
132
190
130
DISPLAY UNIT
242
CALCULATION OF STATISTICS AND SIMILARITY SCORES FIG. 4 = A LINE OF STUDY (5) INTERPOLATED ALONG A PATH THROUGH 4 ICONS (1, 2, 3, 4) ILLUSTRATING THE AUTOMATIC CALCULATION OF VELOCITY DIRECTIONS TANGENT TO THE LINE OF STUDY FIG. 5 ILLUSTRATING A CLOSED LOOP LINE OF STUDY BY SUPERIMPOSING THE LAST ICON UPON THE FIRST

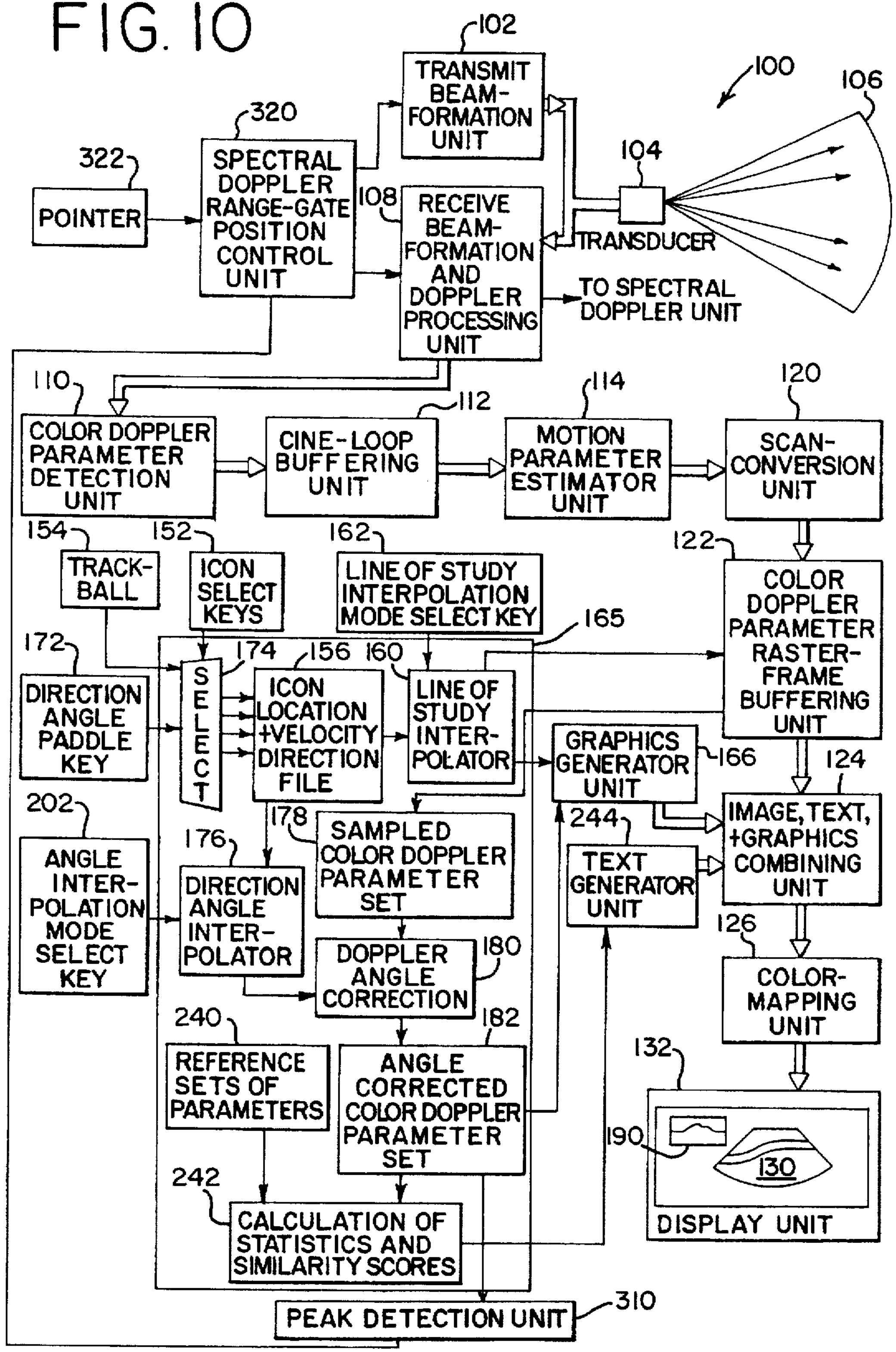
FIG. 10
102
TRANSMIT BEAM-FORMATION UNIT
100
106
320
322
POINTER
SPECTRAL DOPPLER RANGE-GATE POSITION CONTROL UNIT
108
RECEIVE BEAM-FORMATION AND DOPPLER PROCESSING UNIT
104
TRANSDUCER
TO SPECTRAL DOPPLER UNIT
110
COLOR DOPPLER PARAMETER DETECTION UNIT
112
CINE-LOOP BUFFERING UNIT
114
MOTION PARAMETER ESTIMATOR UNIT
120
SCAN-CONVERSION UNIT
154
TRACK-BALL
152
ICON SELECT KEYS
162
LINE OF STUDY INTERPOLATION MODE SELECT KEY
122
COLOR DOPPLER PARAMETER RASTER-FRAME BUFFERING UNIT
165
172
DIRECTION ANGLE PADDLE KEY
SELECT
174
156
ICON LOCATION +VELOCITY DIRECTION FILE
160
LINE OF STUDY INTER-POLATOR
GRAPHICS GENERATOR UNIT
166
124
IMAGE, TEXT, +GRAPHICS COMBINING UNIT
202
ANGLE INTER-POLATION MODE SELECT KEY
176
DIRECTION ANGLE INTER-POLATOR
178
SAMPLED COLOR DOPPLER PARAMETER SET
244
TEXT GENERATOR UNIT
126
DOPPLER ANGLE CORRECTION
180
COLOR-MAPPING UNIT
240
REFERENCE SETS OF PARAMETERS
182
ANGLE CORRECTED COLOR DOPPLER PARAMETER SET
132
190
130
DISPLAY UNIT
242
CALCULATION OF STATISTICS AND SIMILARITY SCORES
PEAK DETECTION UNIT
310

TWO-DIMENSIONAL ULTRASOUND DISPLAY SYSTEM

This application is a division of Ser. No. 08/620,283 filed Mar. 22, 1996 and now U.S. Pat. No. 5,724,974.

BACKGROUND OF THE INVENTION

This invention relates in general to ultrasound systems and in particular to an improved display system for displaying two dimensional images.

In traditional Doppler imaging and display, the user chooses between color Doppler imaging (CDI) or spectral Doppler imaging (SD). CDI refers to both color Doppler B-mode imaging techniques and color Doppler M-mode imaging techniques. CDI provides a qualitative evaluation of fluid dynamics and tissue motion in a body that is imaged. Thus, CDI techniques do not provide the user with quantitative information. Spectral Doppler imaging, on the other hand, provides the user with quantitative flow information about a single point or position in space. While SD does provide quantitative information on the fluid dynamics and tissue motion imaged, it is also limited in the sense that the information is limited to a single position or point in space. In clinical applications, it is frequently desirable to be able to obtain quantitative information on more than just a single point in space.

One approach to address the above-described need is outlined in U.S. Pat. No. 4,790,322 to Iinuma and "Quantitative Measurement of Volume Flow Rate (Cardiac Output) by the Multibeam Doppler Method," Tsujino et al., *Journal of the American Society of Echocardiography*, September-October 1995, pp. 621–630. In such approach, an ultrasonic transducer is used to steer an ultrasonic beam towards a region of interest of a subject to be measured. The echoes from the region of interest are received, and a Doppler calculation section detects the Doppler shift from the echoes on a line orthogonal with the steering ultrasound beams and echoes. The speed of blood flow in the region of interest is then calculated from the Doppler shift signal. The requirement that the line imaged be orthogonal to the ultrasound steering beam limits the number of clinical applications in which this measurement may be used. It may be impossible for the sonographer/operator to position the line imaged so that it is orthogonal to the ultrasound steered beam. If the line imaged is not orthogonal to the ultrasound steering beams, the flow measurement may be invalid.

The Acuson 128XP system employs two color calipers on a display screen. The velocities at the calipers can be displayed on the screen, as can the difference between these velocities and the distance between the calipers.

None of the conventional or proposed display systems for displaying Doppler information is entirely satisfactory. It is therefore desirable to provide an improved display system with improved characteristics over the above-described systems.

SUMMARY OF THE INVENTION

This invention is an improvement on existing systems for display and quantification of ultrasound information. This invention provides quantitative information not only at a single position or point in a two dimensional ultrasound image, but at three or more points on a line of study on the image.

Thus one aspect of the invention is directed towards a display method for use in an ultrasound system, comprising the steps of placing measuring icons at any two or more desired positions on a two-dimensional ultrasound image; selecting a line of study based on the positions of the icons and displaying information related to the ultrasound image for three or more points on said line of study.

Another aspect of the invention is directed towards a display tool for use in an ultrasound system, comprising user interface means for placing measuring icons at any two or more desired positions on a two-dimensional ultrasound image; means for selecting a line of study based on the positions of the icons and means for displaying information related to said ultrasound image for three or more points on said line of study.

Still one more aspect of the invention is directed to a display method for use in an ultrasound system comprising the steps of defining a line of study at any location on a two-dimensional ultrasound image obtained using ultrasound signals along ultrasound lines, said line of study having at least a portion that is not orthogonal to an ultrasound line; and displaying information related to said ultrasound image for at least three points on said line of study.

One more aspect of the invention is directed to a display tool for use in an ultrasound system comprising user interface means for defining a line of study at any location on a two-dimensional ultrasound image obtained using ultrasound signals along ultrasound lines, said line of study having at least a portion that is not orthogonal to an ultrasound line; and means for displaying information related to said ultrasound image for at least three points on said line of study.

Another aspect of the invention is based on the recognition that, in order to implement the sampling of data along a line of study in a two-dimensional image, it is preferable to first scan convert the data of the image prior to the sampling of the data and the display of information. Thus, another aspect of the invention is directed towards a method for providing information on a line of study on a two-dimensional image, comprising the steps of providing scan converted data; obtaining a study data set by sampling at a plurality of locations along the line of study; and displaying information related to said study data set.

Still another aspect of the invention is directed towards a tool for displaying information involving a line of study on a two-dimensional image, comprising means for providing scan converted data; means for obtaining a study data set by sampling at a plurality of locations along the line of study; and means for displaying information related to said study data set.

One additional aspect of the invention is based on the realization that if velocity direction angle information is input at two or more points on a line of study on the image, then velocity direction angles may be provided for all other points along the line of study by calculation and interpolation. In this manner, the user may specify the velocity direction angles for a fewer number than all of the points on the line of study for which information is to be displayed. Thus, another aspect of the invention is directed towards an ultrasound interpolation method comprising the following steps obtaining a two-dimensional ultrasound image containing motion data; inputting velocity direction angle information for a line of study on the image; and interpolating and providing velocity direction angles for performing Doppler angle corrections to information related to said motion data at points along the line of study in response to said velocity direction angle information.

Another aspect of the invention is directed towards an ultrasound color interpolation system comprising means for obtaining a two-dimensional image containing motion; user interface means for inputting velocity direction angle information for a line of study on the image; and interpolating means for providing velocity direction angles for information related to said motion at points along the line of study in response to said velocity direction angle information.

BRIEF DESCRIPTION OF THE DRAWINGS

FIG. 1A is a schematic view of an ultrasound two-dimensional image useful for illustrating the preferred embodiment of the invention.

FIG. 1B is a graph of a velocity profile for the ultrasound image in FIG. 1A.

FIG. 1C is a numeric read out of a calculated parameter for the ultrasound image of FIG. 1A.

FIG. 3 is a block diagram of an ultrasound system for two-dimensional image acquisition and display to illustrate the preferred embodiment of the invention.

FIG. 6 illustrates the perpendicular velocity direction angle generation mode of the invention.

FIG. 10 is a block diagram of an ultrasound system for two-dimensional image acquisition and display to illustrate another aspect of the preferred embodiment of the invention.

For simplicity in description, identical components are identified by the same numerals in this application.

DETAILED DESCRIPTION OF PREFERRED EMBODIMENTS

Figure 2B:
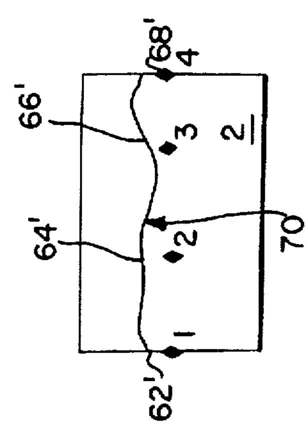
FIG. 2B is a graph of an acceleration profile useful for illustrating the motion of the heart-muscle wall of FIG. 2A.

For purposes of describing the preferred embodiments, the terms used have the meanings below.

I. Definitions

Two-dimensional image: an ultrasound image having two dimensions both of which are in distance or represent distances.

Ultrasound line: lines directed along the centers of ultrasound beams, where ultrasound beams are very narrow directional beams in the current state-of-the-art for medical ultrasound imaging systems. See page 72 of *Doppler Ultrasound, Physics, Instrumentation, and Clinical Applications,* John Wiley & Sons, 1989. This definition is applicable for ultrasound systems employing either Doppler shift or time shift for motion detection.

Line of study: a line of any shape or extent on an ultrasound display where the line may or may not intersect itself or form a closed loop.

Defining a line of study: a line of study may be defined by first choosing two points and then defining the line as a path that is placed on the two-dimensional image as a function of the two points, or by drawing the line on the image by means such as a trackball, mouse, tablet, light pen or other drawing devices.

Color Doppler parameters: mean velocity, variance of velocity, energy and acceleration of tissue or blood flow in a body imaged.

Acoustic grid: a format for ultrasound information organized as samples taken at a set of distinct depths along each of a set of distinctly-aimed ultrasound lines.

Acoustic frame: set of measures detected from ultrasound echo information at each of a set of distinct depths along each of a set of distinctly-aimed ultrasound lines.

Motion data: an acoustic frame in which the measures are of any subset of a set of color Doppler parameters.

Display grid: a format for ultrasound information organized as samples at a set of horizontal or vertical locations along each of a set of TV raster lines.

Scan conversion: image processing step which converts information from the acoustic grid to the display grid.

Display frame: set of measures derived from one or more acoustic frames, and organized in the display grid, by scan-conversion.

Study data set: the set of measurements of ultrasound return at points along a line of study in a display frame.

Reference study data set: a study data set that has been saved and then brought back for comparison with another study data set.

Angle: in this description, angles are measured counterclockwise from a descending vertical line in the display grid; units are radians, although this detail does not enter into the description.

Minimum-arc angle bisection: given two direction angles, the direction angle of the vector which is the vectorial sum of two equal-magnitude vectors, one each in the direction of the direction angles being bisected.

Velocity direction angle: at a point in the display grid, the angle in which motion (tissue or fluid) is proceeding.

Velocity direction: at a point in the display grid, the direction in which motion (tissue or fluid) is proceeding.

Velocity direction angle correction: at a point in the display grid which corresponds approximately to a small sample volume in the body: a mathematical operation to correct for the lessening of measured mean velocity, variance, energy, and acceleration parameters, due to the angle between the mean direction of motion in the sample volume and the direction of the ultrasound line through that sample volume.

Ultrasound image having motion data: an ultrasound image with measures of motion of tissue or blood therein.

Information related to motion data: a set of features on a two-dimensional ultrasound image describing or indicating characteristics of tissue motion or blood flow in the image.

This invention may also be used to display information based on time shifted information in a system such as that described in U.S. Pat. No. 4,928,698 and the article "Time Domain Formulation of Pulse Doppler Ultrasound and Blood Velocity Estimation by Cross-Correlation," by Bonnefous et al., *Ultrasonic Imaging*, 8, 73–85 (1986). Thus the information related to motion data defined above can be derived from either Doppler shift or time shift data.

II. Detailed Description of the Drawings FIG. 1A is a schematic view of an ultrasound two-dimensional image of a blood vessel with left-to-right flow and a line of study to illustrate the preferred embodiment of the invention. As shown in FIG. 1A, image 20 is obtained from a sector ultrasound scan where the ultrasound beams are illustrated by lines 22. A blood vessel 24 is shown in image 20 and a line of study 26 is shown cutting across the blood vessel so as to take a cross-sectional image of the blood flow in the vessel along the line of study. In the preferred embodiment, the line of study 26 may be specified by means of two measuring icons 30 and 32 and the points on the line of study 26 can be arrived at by interpolation in the manner described below. In the embodiment illustrated in FIG. 1A, the line of study 26 is a straight line segment connecting the two icons 30, 32. Alternatively, the line of study may be curved and need not pass through the icons 30, 32 but may be defined as a function of the positions of the icons, such as at desired displacements from the icons.

The icons 30, 32 may be placed by the user at any two positions in the image 20 displayed so that the line of study 26 may also be placed at any location and any orientation on the image. Alternatively, a line of study may be placed on the display screen without using icons, such as by drawing a line at any location, of any shape and orientation on the screen by an input means such as a light pen, trackball, mouse, tablet or other drawing input devices.

As is evident from FIG. 1A, the line of study 30 is at an acute angle to the scan beam 22. In other embodiments, the line of study may have at least one portion that is not orthogonal to an ultrasound line, such as one of the ultrasound lines for scan beams 22. FIG. 1B is a graphical illustration of a velocity profile across the vessel 24 along the line of study 26 of FIG. 1A, where the vertical axis is velocity and the horizontal axis is distance from icon 30. In reference to FIGS. 1A and 1B, the velocity at the left end 30' of the horizontal axis in the profile graph 40 is the velocity at the beginning of the line of study at icon 30, and the velocity at the right end 32' of the horizontal axis in the profile graph 40 is that at the end of the line of study at icon 32; the velocities at points between 30', 32' in graph 40 are those at points between icons 30, 32.

The velocity profile 40 shown in FIG. 1B is also displayed on the screen as well as image 20, so that the user is able to correlate points on the velocity profile with image 20 for diagnostic and other purposes. In contrast to spectral Doppler imaging, velocities at a plurality of points along the line of study are shown in profile 40, instead of only at a single point in space. In some applications, it may be adequate to display the velocity values at three points along the line of study, where such three points may or may not include the end points; such and other variations are within the scope of the invention. FIG. 1C illustrates a numerical readout of a quantity calculated from the data in the image 20, where such data may be that at a point on the line of study or data of a region in the image; preferably, such readout is displayed on unit 132 together with the image 20 of FIG. 1A and the profile of FIG. 1B.

Each of the two icons 30, 32 are shown as a small diamond shape graphics figure distinguishable by a small numeric label indicating an order of the icons, such as "1" and "2" in FIG. 1A; the same ordering notation is used in other figures of this application. An equally preferable set of icons consists of an "X" icon and "+" icon, as in the current implementation of the color calipers feature on the Acuson 128XP system. As discussed below, each icon has a velocity-direction indicator vector, which appears like an arrow passing through the center of the icon. Icon 30 has velocity-direction indicator vector 30', and icon 32 has velocity-direction indicator vector 32'.

Figure 2A:
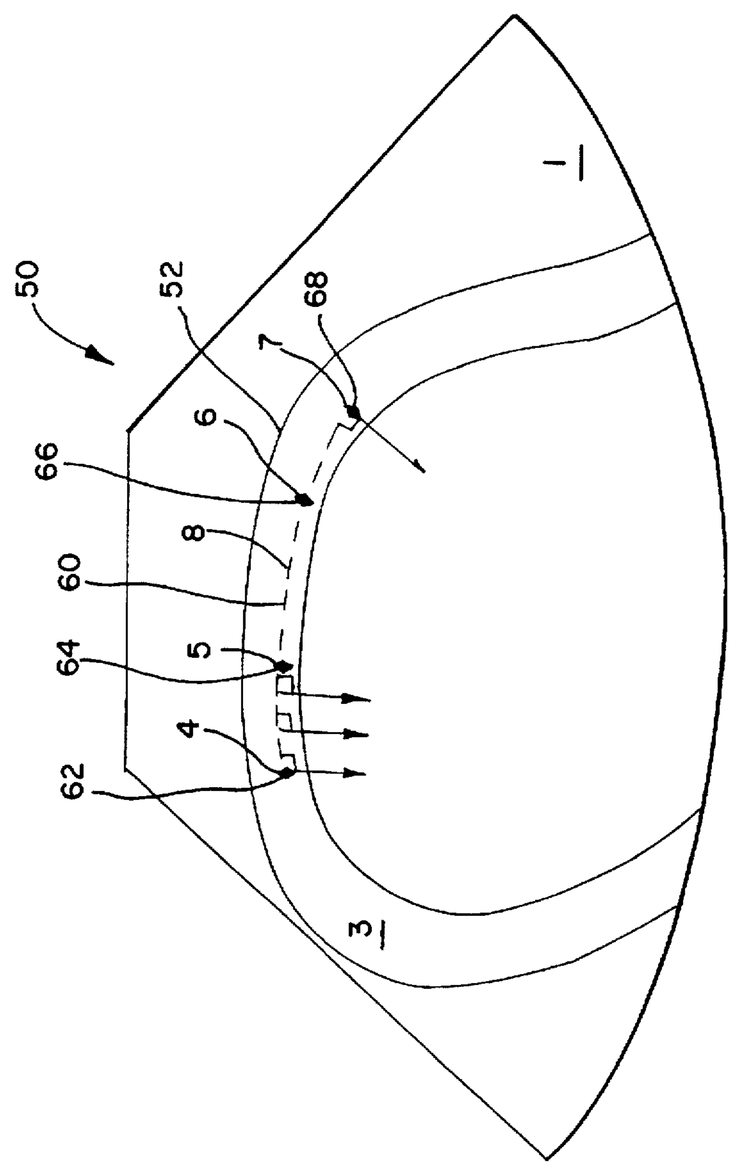
FIG. 2A is a schematic view of an ultrasound two-dimensional image of a heart-muscle wall to illustrate the preferred embodiment of the invention.

FIG. 2A is a schematic view of an ultrasound image 50 of a heart-muscle wall 52 to illustrate the invention. Instead of using two measuring icons, four measuring icons are shown in FIG. 2A, located in wall 52. When the user selects the icons for display, the icons are selected preferably as an ordered set. As shown in FIG. 2A, the icons 62, 64, 66 and 68 form an ordered set (labeled 4, 5, 6, 7) in such order. FIG. 2B is a graphical illustration of a velocity profile across a line of study drawn through the four icons. The effect of the order of the four icons in an ordered set is such that they are arranged in the same order in FIG. 2B in the velocity profile so that the value of the velocity shown in the graph 70 corresponds to corresponding spatial locations on the line of study. Thus, the values of the velocity at point 62'–68' in FIG. 2B are the velocity values at corresponding icons 62–68 in FIG. 2A. The same is true for velocities at points between any two adjacent pairs of points such as 62', 64' and the points between two adjacent icons such as icons 62–64. In this manner, there is a direct spatial correlation between velocity profile 70 and the line of study 60 for clinical analysis. In the preferred embodiment, the line of study 60 is a directed line drawn through the invoked icons, according to the order of the icons in the ordered set. Thus, line of study 60 is preferably a directed line drawn beginning from icon 62 through icon 64, then through icon 66 and then through icon 68. If the user decides to remove one icon, such as icon 66, then the line of study would proceed from icon 62 to icon 64 and to icon 68. The order selected by the user then specifies the order of the corresponding points on the profile 70 for easy clinical comparison.

FIG. 3 is a block diagram of an ultrasound system for acquiring color Doppler data and displaying color Doppler information to illustrate the preferred embodiment of the invention. As shown in FIG. 3, system 100 includes a transmit beam-formation unit 102 that controls transducer 104 for generating ultrasound signals scanning a region of interest in a body to be imaged in one of several possible formats, such as linear, steered linear, sector, VECTOR® and curved linear array formats. Systems using the VECTOR® format are described in U.S. Pat. Nos. 5,148,810; 5,235,986 and 5,261,408. A suitable transmit beamformer is the Acuson 128XP beamformer; other suitable systems are described in U.S. Pat. No. 5,675,554 which is incorporated herein by reference.

The echo return of the ultrasound signals from the region of interest is sensed by transducer 104 and transmitted to receive beam-formation and Doppler processing unit 108 which process the received data and provide such data to a Spectral Doppler unit (not shown) and a B-mode unit (not shown). A suitable Spectral Doppler unit is the one used in Acuson 128XP; other suitable ones are described in U.S. Pat. No. 5,555,534 filed May 2, 1995 which is a CIP of Ser. No. 08/286,648, filed Aug. 5, 1994 and now abandoned, which are incorporated herein by reference. A suitable receive beamformer is the one used in Acuson 128XP; other suitable ones are described in allowed U.S. patent application Ser. No.: 08/432,615 filed May 2, 1995 which is a CIP of Ser. No. 08/286,658, filed Aug. 5, 1994 and now abandoned which are incorporated herein by reference. In addition, unit 108 provides the processed echo data to color Doppler parameter detection unit 110 which performs high pass filtering and parameter detection by a suitable method such as autocorrelation and provides the detected parameters to cine-loop buffering unit 112 where such information is stored. Where autocorrelation is used for parameter detection, preferably some of the autocorrelation coefficients are stored in unit 112. As an alternative embodiment, the motion data is acquired according to the time shift technique by Bonnefous in U.S. Pat. No. 4,928,698 and stored in unit 112.

In the context of color Doppler imaging system 100, data on motion in the color Doppler image is estimated by estimator unit 114 which estimates color Doppler parameters including mean velocity, variance, energy and acceleration. The estimated parameters in acoustic frames are then scan converted from the acoustic grid for the ultrasound samples to display grid by scan conversion unit 120 to form display frames. A suitable scan converter is the Acuson 128XP scan converter; other suitable converters are described in U.S. Pat. No. 5,563,810 filed May 3, 1995, which is incorporated herein by reference. The scan converted estimated parameters are then stored in the color Doppler parameter raster-frame buffering unit 122 which stores one or preferably two raster frames of the image of the region of interest 106.

A display frame of the region may be of the type such as shown in FIGS. 1A and 2A. Such frame is then supplied to the text and graphics images combining unit 124 which combines such frame with other inputs described later. The combined data is then supplied to a color mapping unit 126 which derives display information therefrom to be displayed as image 130 on the display unit 132.

The portion of system 100 for selecting and placing icons in the line of study will now be described. Icon select keys 152 enable a user to activate the icons that will be used and trackball 154 enables the user to move the icon and place it at the desired location on the image 130. Of course, one of ordinary skill in the art will recognize that as an alternative, a mouse, a tablet, joystick or other positioning device can be used. In the preferred embodiment, the user may position up to ten icons on the two-dimensional Doppler image 130. Numeric keys 0 through 9 on the QWERTY keyboard may be used for this purpose. While these keys are also used for other functions, system 100 supports arbitrated sharing of the keyboard. Pressing any icon's key invokes and activates its corresponding icon. When an icon is invoked, it is displayed somewhere on the two-dimensional image 130. When an icon is activated, trackball movements by means of trackball 154 would move the icon around on image 130. Preferably only one icon is activated at any time. Pressing any icon key corresponding to an invoked icon makes that icon the active icon and deactivates any active icon. Pressing an icon key corresponding to the active icon removes (uninvokes) that icon.

Line of Study

Figure 4:
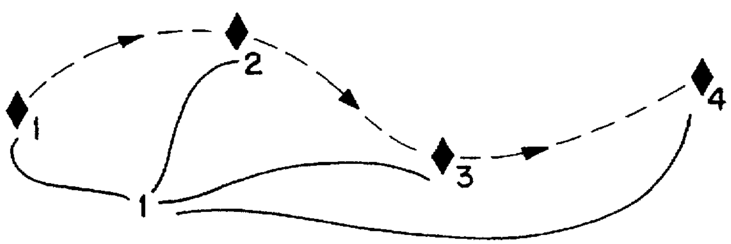
FIG. 4 is a schematic view of a line of study interpolated between four icons to illustrate the invention.
Figure 5:
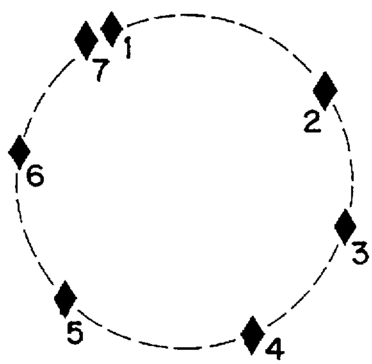
FIG. 5 is a schematic view of a closed loop line of study to illustrate the invention.

In the preferred embodiment, the line of study is specified at 128 points of the line; such set of points is referred to below as a discrete line of study (DLOS). It will be evident to those of ordinary skill in the art that more or fewer points may be specified for the line of study. This line may be a single straight-line segment, such as that between two icons, a piece-wise linear connective path connecting a plurality of icons, or connective path of piece-wise cubic curves connecting the plurality of icons. As noted above, the line of study is drawn beginning from the icon designated as the first icon by the user through the icon designated by the user as the second icon and so on in such order until the last icon designated by the user is reached. As shown in FIGS. 4 and 5, the line of study may or may not form a closed loop.

When being processed by system 100, the line of study is a set of 128 points (Xi,Yi), where i=0, 1, 2, . . . , 127, in the display or "raster" grid space, constructed by interpolation from the icon locations designated by the user, which is a sparse set of points (Xj,Yj), j=0, 1, . . . M−1 in this same space, with $M \leq 10$ in the preferred embodiment.

Thus, the icons activated and placed at the desired locations on image 130 by means of keys 152 and trackball 154 by the user are stored in the icon location and velocity direction file 156 where such stored data are interpolated by line of study interpolator 160 into the 128 points of the line of study. By means of line of study interpolation mode select key 162, the user may select between different options such as linear or curved line segments, to connect the icons in order to form the line of study. The coordinates of the 128 points in the line of study are then supplied by interpolator 160 to graphics generator 166 for generating the image of the line of study which is supplied to combining unit 124. The combining unit then combines the image of the line of study and the raster-frame data from buffering unit 122 so that the image 130 displayed includes the line of study at the designated locations by the user.

Study Data Set

The interpolated points on the line of study are then used as addresses by interpolator 160 to fetch the color Doppler parameters at such points to be supplied as a study data set to the sampled color Doppler parameter set 178 unit. The unit 178 in turn provides the data set to Doppler angle correction block 182 for angle correction.

Velocity Direction Angles

System 100 provides the capability for the user to designate velocity direction angles along which motion is to be detected. This is accomplished by means of a single paddle-switch 172. Pressing up on this switch causes the velocity-direction angle for the active icon to increment preferably in a counterclockwise direction in one degree increments from 0°–359° and then back to 0°. Pressing down causes this angle to decrement (clockwise rotation). System 100 also provides three different velocity-direction angle modes for selection by the user. In one of the three modes called the manual mode, the user uses the paddle-switch to indicate a velocity direction at each icon. This is illustrated, for example, in FIG. 1A. As shown in FIG. 1A, the velocity direction angle is indicated by line. 30a referred to herein as the velocity direction indicator vector, which appears as an arrow passing through the center of the icon 30. Icon 32 has a similar vector 32a passing through its center.

In the event that the blood flow in vessel 24 has diverged into different directions upon passing the line of study 26, it may be desirable for the user to orient vectors 30a, 32a so that the velocities displayed by monitor 132 at different points along the line of study are those substantially along the directions of flow at such points. While icons 30, 32 are not in the blood vessel 24, the direction of flow along points in the line of study within the blood vessel 24 as well as other points between the two icons are arrived at by means of interpolation, such as linear interpolation. In other words, the velocity direction indicator vector for each point on line 26 between the two icons may be arrived at by interpolating between the velocity direction angles of the two vectors **30*a*, 32*a* as a function of the ratio of the distance between such points and icon 30** to the distance between the two icons. In this manner, the velocity profile arrived at will give the clinician a more accurate representation of the velocities along the line of study.

The direction angle input by the user is passed through the select multiplexer 174 and stored in file 156 which provides this data to the direction angle interpolator 176 which performs an interpolation process such as the linear one described above. Interpolator 176 provides the interpolated direction angles along the line of study to Doppler angle correction unit 180. As indicated above, the line of study interpolator 160 provides the coordinates of points on the line of study to buffering unit 122 for retrieving the sampled color Doppler parameter data at such points on the line of study and provides such data to correction unit 180. Correction unit 180 then corrects the data received from block 178 in accordance with the direction angle information received from interpolator 176.

Correction unit 180 functions as follows. Where the ultrasound scan lines are in the linear or steered linear format, the ultrasound lines are all parallel and at a constant angle to the line of study and may be ignored so that no correction need to be made. However, in the sector, VECTOR® and curved linear array formats, angle correction needs to be made dependent on the Doppler line angle which is computed as follows. At each point (Xi,Yi) in the line of study, the Doppler line angle in the display raster XY coordinate space is given by arctan((Xi-Xapex)/(Yi-Yapex)) where (Xapex, Yapex) are the display coordinates of the apex of the scan format. The velocity correction angle at any point on the line of study is then the difference between the Doppler line angle at that point and the velocity direction angle at that point indicated by Interpolator 176.

The angle corrected color Doppler parameter data is then provided by unit 180 to angle corrected color parameter set storage 182 which provides such data to graphics generator unit 166 for generating graphics data for display. Such angle corrected data is then combined by combining unit 124 and converted by unit 126 into the graphical plot 190 on display unit 132.

Where the data on motion stored in unit 112 of FIG. 3 is time shift information instead of color Doppler parameters, a process similar to the one described above can be readily implemented. Such and other variations are within the scope of the invention.

Automatic Velocity Direction Modes

(Tangent and Perpendicular)

Figure 6:
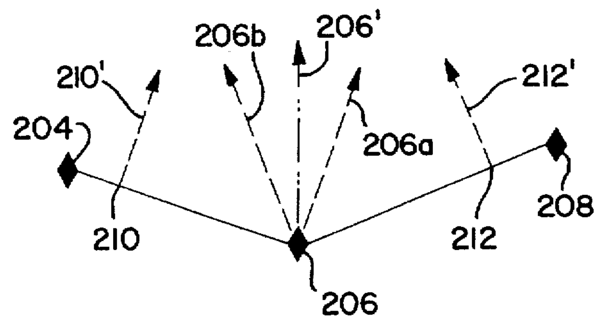
FIG. 6 is a schematic view of two straight line segments connected at an icon where adjacent portions of the two line segments are at different slopes to illustrate one method of computing the velocity direction angle for illustrating the invention.

In addition to the manual mode for selecting directional angles, system 100 also enables an automatic tangent or an automatic perpendicular velocity direction mode to be selected by the user using angle interpolation mode select key 202. By means of key 202, the user can select between the manual mode, the automatic tangent velocity direction mode or the automatic perpendicular velocity direction mode. FIG. 6 is a schematic view of the three icons 204, 206 and 208, where the line of study includes two straight line segments, one connecting icons 204, 206 and the other connecting icons 206, 208. As shown in FIG. 6, the two line segments are straight lines, so that there is a change in direction between the two line segments at icon 206. If the user selects the automatic perpendicular mode, then the direction angle in interpolator 176 will, for each point on each of the line segments, select a direction perpendicular to such line segment as the velocity direction indicator vector of such point. Thus, in reference to FIG. 6, at point 210, interpolator 176 will select the velocity direction angle vector 210' for defining the direction angle and provide such information to correction unit 180. It is noted that the direction of such vector remains the same for all points between icons 204 and 206.

At point 212 on the line segment connecting icons 206, 208, the direction angle is defined by vector 212', and the direction of such vector remains constant at points between the two icons 206, 208. However, at icon 206, the direction of such vector becomes undefined. In the preferred embodiments, this is defined by means of minimum-arc average, or bisection, of the angles of the normals to the two line segments meeting at the icon 206. In other words, the direction angle at icon 206 is defined by vector 206' which bisects the angle between vector **206*a* parallel to vector 210' and vector 206*b* parallel to vector 212'**.

In general, given two direction angles, there are two ways to bisect the angles, or take an "average" of the two angles. Minimum-arc or bisection gives the direction angle which is the direction of the vectorial sum of two unit vectors, one in each of the direction angles being bisected.

Figure 7:
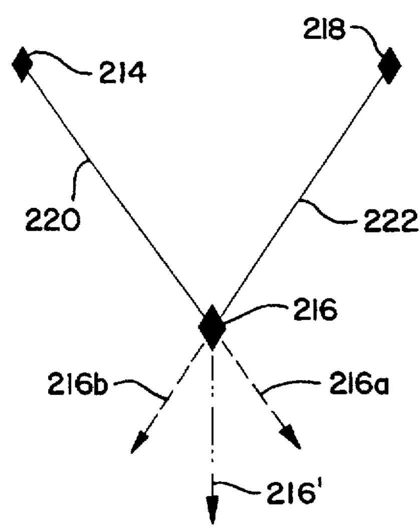
FIG. 7 is a schematic view of two straight line segments to illustrate how to derive the velocity direction angle in the tangent mode to illustrate the invention.

The automatic tangent mode is illustrated in FIG. 7. Again, the line of study is defined by three icons 214, 216, 218, where the two icons 214, 216 are connected by a straight line segment as are icons 216, 218. In a tangent mode, for each point on each segment, interpolator 176 automatically selects a velocity direction angle vector which is tangent to such line of study segment at such point. Thus, in FIG. 7, the direction angle vectors along line 220 are along the line pointing from icon 214 to icon 216 and the direction angle vectors along line 222 are along the line pointing from icon 216 to icon 218. Again, there is an abrupt change in direction of the line of study between the two line segments at icon 216. As in FIG. 6, the minimum-arc average or bisection is taken at the icon so that the velocity direction indicator vector 216' at the icon bisects the angle between vector **216*a* tangent to the line segment between icons 214 and 216 at icon 216 and vector 216*b* which is tangent to the line segment between icons 216, 218 at icon 216**.

As will be noted from the above description, if the user selects one of the two automatic modes, the direction angle is automatically computed once the user activates and places the icons and presses the selected keys 162, 202.

Reference Study Data Sets

In some applications, it may be useful to compare the color Doppler parameter data estimated to statistics and display the comparison in display 190. For example, display information derived from the data obtained from imaging a person presently may be compared to display information derived from similar data from an image of the same person taken at an earlier time. Alternatively, the reference study data set may comprise similar data from persons with normal or diseased conditions. Such reference study data sets from the same or different persons may be stored in reference sets of parameters storage 240 and provided for the calculation of statistics and similarity scores according to preset criteria in block 242. Such statistics and similarity scores are then supplied to the text generator unit 244 for generating a quantity such as a number to indicate the results of such comparison. Such quantity is combined by combining unit 124 with the inputs from units 122, 166, converted by color mapping 126 into a display of such quantity in profile display 190.

Data on motion derived from the current and stored study data sets may also be derived from time shift information and displayed for systems such as that described in U.S. Pat. No. 4,928,698.

Display of Estimated Spectra Over Distance and Time

Figure 8A:
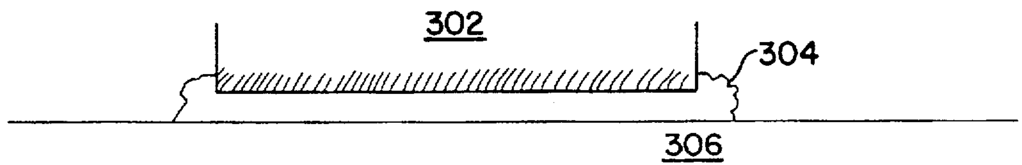
FIG. 8A is a cross-sectional view of a portion of a transducer, a coupling agent and a surface of a body to be imaged to illustrate the invention.
Figure 8B:
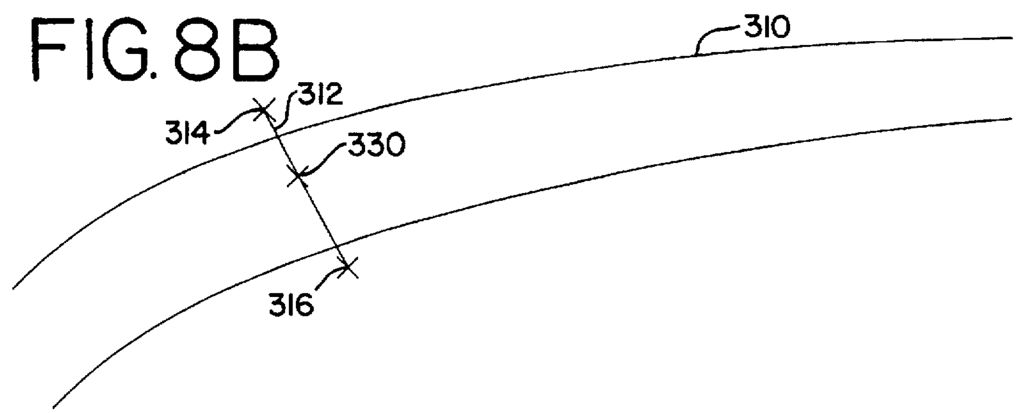
FIG. 8B is a schematic view of a blood vessel, a line of study placed across it and a range gate to illustrate the invention.
Figure 8C:
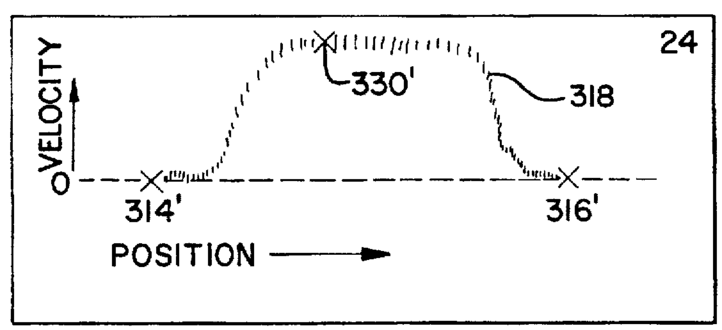
FIG. 8C is a graphical illustration of the velocity profile along the line of study of FIG. 9B to illustrate the invention.

FIG. 8A is a schematic view of a portion of a transducer 302 coupled by a coupling agent 304 to a body 306 to be imaged. Body 306 contains a conduit through which a fluid flows, such as a blood vessel 310 containing blood flow. FIG. 8B is a schematic view of the blood vessel 310 in body 306 where the line of study 312 is defined by and connects icons 314, 316. FIG. 8C is a graph of the estimated spectra at each of the points of the line of study 312. As shown in FIG. 8C, the left end point 314' corresponds to icon 314 of FIG. 8B and the right end point 316' corresponds to icon 316 of FIG. 8B.

As also shown in FIG. 8C, the horizontal axis indicates position or distance from icon 314 along the line of study, and the magnitude of the vertical dimension indicates the velocity along the velocity direction vector at such position on the line of study. In addition, the variance of velocity at such point is also shown by the vertical thickness of the curve 318. The energy of the blood flow at such point can be displayed by either a luminance or color modulation of the curve 318. In addition to the magnitude of the vertical dimension and the vertical thickness of the curve 318, such luminance or color also gives a quantitative measure of motion in the image.

If the distribution of velocities in the motion being measured is substantially Gaussian, the velocity spectrum can be estimated from the mean velocity, energy, and variance estimates provided by the apparatus described above, or equivalent means, according to the equation:

$$\text{Spectrum Power }(V) = \text{Energy} \times e^{-\frac{(V - \text{Mean Velocity})^2}{2\,\text{Variance}}}$$

Figure 8D:
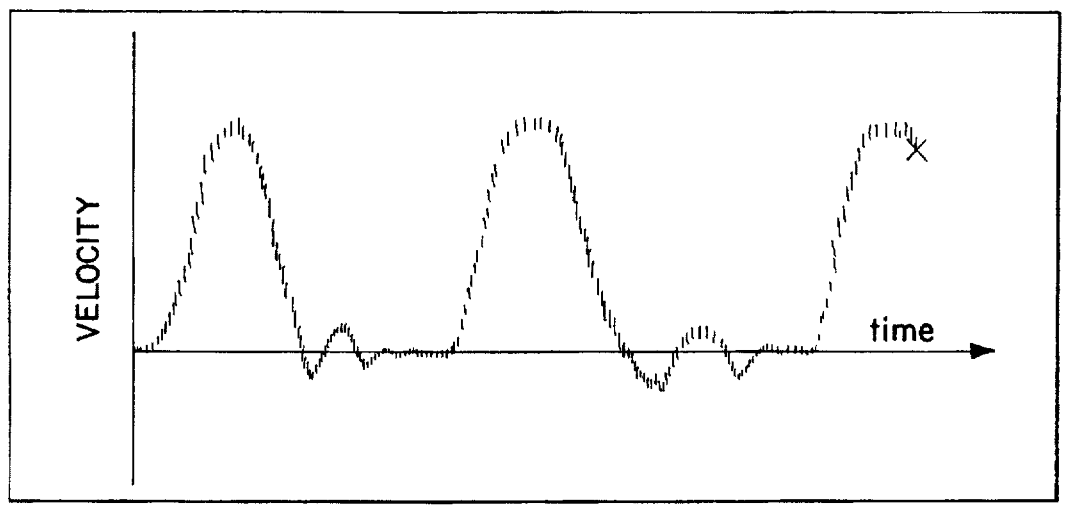
FIG. 8D is a spectral strip illustrating the full spectra at points along the line of study of FIG. 9B to illustrate the invention.

These estimated spectra can be computed and displayed corresponding to any point on the motion image. In this preferred embodiment these points are the points along the line of study selected by the user. Note that this display provides a spectrograph, similar in appearance to the conventional spectral Doppler strip display or "sonogram", but replacing the time axis of that display with a spatial axis, as shown in FIG. 8C. A spectral strip similar to the conventional spectral Doppler strips but employing estimated color Doppler parameters may be displayed, as shown in FIG. 8D, where the parameters are displayed as a function of time at a selected range gate position, such as 330 in FIG. 8B.

Figure 9A:
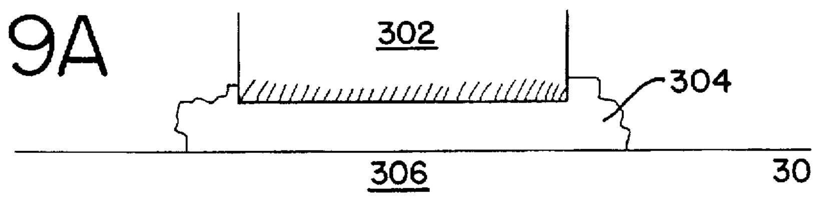
FIG. 9A is a cross-sectional view of a portion of a transducer, a coupling agent and a surface of a body to be imaged to illustrate the invention.
Figure 9B:
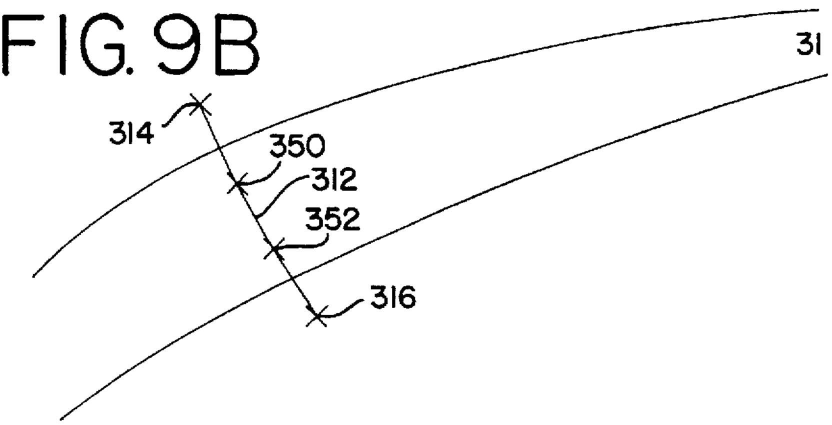
FIG. 9B is a schematic view of a blood vessel, a line of study across the vessel and two range gates to illustrate the invention.
Figure 9C:
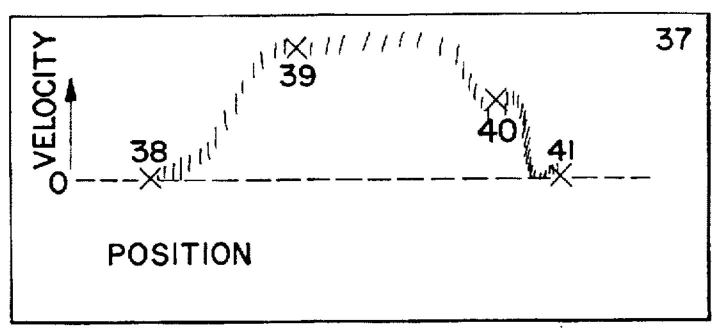
FIG. 9C is a spectrum of the ultrasound image at points along the line of study of FIG. 11B.
Figure 9D:
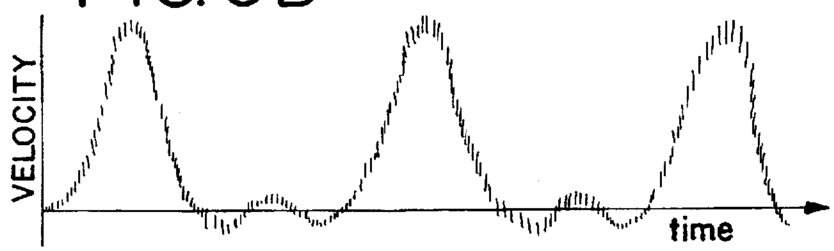
FIGS. 9D and 9E are two spectral strips showing the spectra at the two range gates of FIG. 9B.
Figure 9E:
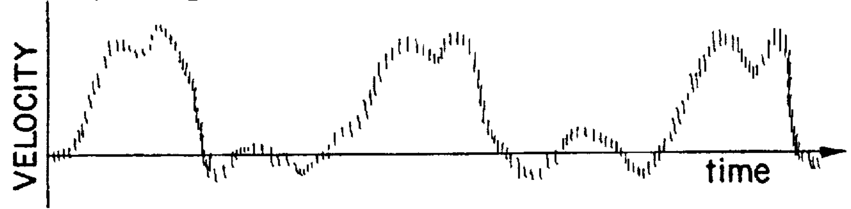

Instead of observing the spectral strip at only a single range gate location, it is also possible to observe the change in the spectra over time at two different range gate positions 350 and 352 in FIG. 9B, where the spectral strips at such locations are shown in FIGS. 9D, 9E.

Coupling to Spectral Doppler Range Gate Positioning

According to another aspect of this invention, velocity information gathered along the line of study can be used to assist in the placement of a spectral Doppler range gate. The intent of this aspect of this invention is to provide the user with easier and more capable ways to position the range gate precisely at the places in blood flow or tissue motion corresponding to points in a velocity profile curve, and to provide a tracking system to keep the range gate positioned at a peak velocity location, along a specified line of study. FIG. 10 illustrates the required apparatus, shown as an addition onto the apparatus illustrated in FIG. 3 and described above.

In reference to FIG. 10, in a manual mode of operation, the user can manipulate, via a pointing device or other means 322, the placement of a marker 330 upon a velocity profile curve 312 in FIG. 8B. The horizontal coordinate of this marker 330' in the velocity profile curve coordinates of FIG. 8C corresponds with a point 330 (Xg, Yg) along the line-of-study 312.

During live motion imaging, and when the study data set includes velocity information, an automatic range gate positioning feature may be selected in which a peak-detection unit 310, continuously monitors the study data sets and finds from these the time-series of points (Xg, Yg) in the discrete line of study at which the velocity takes on a maximum value. In the preferred embodiment, peak detection unit 310 is implemented as a software algorithm.

The range-gate position (Xg, Yg), whether determined by the manual or automatic mode, is directed to the spectral Doppler range gate position control unit 320. The point (Xp, Yp) is transformed as necessary to acoustic grid coordinates, and is used to select the spectral Doppler ultrasound line, depth of transmit focus, and depth to the center of the range gate.

The block 165 is preferably implemented in software; however, it will be understood that hardware implementations are also possible. While it is possible to implement block 165 using data from the acoustic grid directly from buffering unit 112, preferably scan converted data from buffering unit 122 is used instead. This is especially the case if the acoustic grid is one obtained in a vector, sector or curved linear format.

While the invention has been described by reference to various embodiments, it will be understood that different changes and modifications may be made without departing from the scope of the invention which is to be limited only by the appended claims and equivalents thereto.

Attached hereto and made part of this application is a four page appendix which is a code listing of the steps for computing the color parameter values for a profile display.

What is claimed:

1. A display method for use in an ultrasound system comprising the steps of:

defining a line of study on a two-dimensional ultrasound image;

displaying information related to said ultrasound image for at least three points on said line of study; and displaying spectral information related to at least one of said at least three points, said display of spectral information comprising a graph of at least energy, velocity and variance of velocity information at each point along one dimension of the graph.

2. The method of claim 1, wherein said defining step comprises:

placing measuring icons at any two or more desired positions on said two-dimensional ultrasound image; and selecting the line of study based on the positions of the icons.

3. The method of claim 2, wherein said selecting step comprises forming an ordered set of icons from said measuring icons so that the icons have an ordering, and said displaying information related to said ultrasound image for at least three points step comprises displaying said information in reference to the ordering of said icons.

4. The method of claim 2 wherein said selecting step comprises selecting one or more straight line segments joining the two or more positions to be the line of study.

5. The method of claim 1, wherein said displaying information step comprises displaying information related to said motion data in said image.

6. The method of claim 5, wherein said ultrasound image comprises a color Doppler image, and wherein said displaying information related to said ultrasound image for at least three points step comprises displaying information related to at least one color Doppler parameter of said motion data in said color Doppler image.

7. The method of claim 6, wherein said ultrasound image comprises a color Doppler velocity image, and wherein said displaying information related to said ultrasound image for at least three points step comprises displaying said information related to at least one color Doppler velocity parameter.

8. The method of claim 7, wherein said displaying information related to said ultrasound image for at least three points step comprises displaying a velocity profile curve for said line of study.

9. The method of claim 8, wherein said displaying information related to said ultrasound image for at least three points step comprises displaying a variance and/or energy modulated velocity profile curve for said line of study.

10. The method of claim 7 further comprising the step of providing velocity direction angles for information related to said motion data in response to velocity direction angle information, said velocity direction angles corresponding to motion data along the line of study.

11. The method of claim 6, wherein said displaying information related to said ultrasound image for at least three points step comprises displaying a measure of Doppler shift energy related to the motion data in said color Doppler image for said at least three points on said line of study.

12. The method of claim 6, wherein said displaying information related to said ultrasound image for at least three points step comprises displaying an estimate of the variance or of mean velocity of said motion data in the image for said at least three points on said line of study.

13. The method of claim 6, further comprising comparing data related to the color Doppler image to reference color Doppler parameters to derive at least one of said at least one color Doppler parameter.

14. The method of claim 13, said color Doppler image being that of a patient, wherein said comparing step comprises comparing data related to the color Doppler image to reference color parameters related to a color Doppler image of said patient taken at an earlier time.

15. The method of claim 13, said color Doppler image being that of a patient, wherein said comparing step comprises comparing data related to the color Doppler image to reference color Doppler parameters related to color Doppler images of other patients with normal or diseased conditions.

16. The method of claim 6, said color Doppler image including information on tissue motion, wherein said displaying information related to said ultrasound image for at least three points step comprises displaying color Doppler parameters related to tissue motion.

17. The method of claim 6, said color Doppler image including information on blood flow, wherein said displaying information related to said ultrasound image for at least three points step comprises displaying color Doppler parameters related to blood flow.

18. The method of claim 1, wherein said displaying spectral information step comprises displaying a set of estimated spectra, each of said estimated spectra corresponding to one of said at least three points on the line of study.

19. The method of claim 18, wherein said image comprises a color Doppler image, and wherein said displaying spectral information step comprises displaying a set of estimated spectra derived from color Doppler parameters at each of said at least three points on the line of study.

20. The method of claim 19, wherein said displaying spectral information step comprises displaying the set of estimated spectra as a graph having a velocity axis and a distance axis, said graph displayed as the display of information related to said ultrasound image for said at least three points on said line of study.

21. The method of claim 20, wherein said displaying spectral information step comprises displaying the set of estimated spectra using luminance or a color scale to indicate spectral energies.

22. The method of claim 1, further comprising:

placing a first icon at a first position along the line of study; and wherein said displaying spectral information step comprises displaying a spectral strip for said first position.

23. The method of claim 22, further comprising:

placing at least a second icon at a second position along the line of study; and wherein said displaying spectral information step further comprises displaying a spectral strip for said second position.

24. The method of claim 22, further comprising:

moving said first icon to a new position on the line of study; and altering the spectral strip to display information corresponding to the new position.

25. The method of claim 1, further comprising:

determining a target position along the line of study according to a preset criteria;

automatically placing a range gate based on said target position; and wherein said displaying spectral information step comprises displaying a spectral strip corresponding to said range gate.

26. The method of claim 25, wherein said determining step comprises determining the target position along the line of study based on a peak value in a study data set.

27. The method of claim 1 wherein said defining step comprises obtaining said ultrasound image using ultrasound signals along ultrasound scan lines, said line of study having at least a portion that is not orthogonal to one of said ultrasound scan lines.

28. A display tool for use in an ultrasound system, the display tool comprising:

user interface means for defining a line of study on a two-dimensional ultrasound image;

means for displaying information related to said image for at least three points on said line of study; and means for displaying spectral information related to at least one of said at least three points, said display of spectral information comprising a graph of at least energy, velocity and variance of velocity information at each point along one dimension of the graph.

29. The tool of claim 28 wherein said user interface means comprises:

means for placing measuring icons at any two or more desired positions on a two-dimensional ultrasound image; and means for selecting said line of study based on the positions of the icons.

30. The tool of claim 28, wherein said user interface means includes at least two calipers and a trackball.

31. The tool of claim 28, wherein said two-dimensional image comprises a color Doppler image containing motion data, and said means for displaying information related to said image for at least three points comprises a means for displaying information related to color Doppler parameters of said motion data in said color Doppler image.

32. The tool of claim 31 wherein said color Doppler image comprises a color Doppler velocity image, and further comprising interpolating means for providing velocity direction angles for information related to said motion data at points along the line of study in response to velocity direction angle information.

33. The tool of claim 28 wherein said ultrasound image further comprises an image obtained using ultrasound signals along ultrasound scan lines, said line of study having at least a portion not orthogonal to an ultrasound scan line.

34. The tool of claim 28 wherein said means for displaying information related to said image comprises a profile curve related to said line of study.

35. The tool of claim 28 wherein said means for displaying spectral information comprises a display of estimated spectra, each of said estimated spectra corresponding to at least one of said at least three points on the line of study.

36. The tool of claim 35 wherein said image comprises a color Doppler image and wherein said display of estimated spectra comprises a display of estimated spectra at least at each of said at least three points on the line of study.

37. The tool of claim 36 wherein said display of estimated spectra comprises a graph having a velocity axis, a distance axis, and a curve of estimated spectra, said graph displayed as said means for displaying information related to said image for at least three points on said line of study.

38. The tool of claim 37 wherein said estimated spectra comprise a luminance or a color scale to indicate spectral energies.

39. The tool of claim 28 further comprising:

a first icon at a first position along the line of study; and wherein said means for displaying spectral information comprises a means for displaying a first spectral strip display corresponding to said first position.

40. The tool of claim 39 further comprising:

a second icon at a second position along the line of study; and wherein said means for displaying spectral information comprises a second spectral strip display corresponding to said second position.

41. The tool of claim 39 further comprising:

means for moving said first icon to a new position on the line of study; and wherein the first spectral strip display corresponds to said new position.

42. The tool of claim 28 further comprising:

means for determining a target position along the line of study based on preset criteria;

means for placing a range gate position determined based on said target position; and wherein said means for displaying spectral information comprises a spectral strip display corresponding to said range gate position.

43. The tool of claim 42 wherein said preset criteria comprises a peak value in a study data set.

44. The tool of claim 28 wherein said ultrasound image comprises a color Doppler image, and further comprising:

means for storing reference color Doppler parameters; and means for comparing data related to the color Doppler image to said reference color Doppler parameters to derive at least one color Doppler parameter.

45. The tool of claim 44 wherein said ultrasound image corresponds to a patient, and wherein said reference color Doppler parameters comprise color Doppler parameters selected from one of: from a same patient taken at an earlier time, and from another patient with normal or diseased conditions.

46. The method of claim 1 wherein said defining step further comprises obtaining a study data set by sampling said information related to said ultrasound image at a plurality of locations along the line of study.

47. The method of claim 46 wherein said two-dimensional image containing motion data, said study data set containing color Doppler parameters and wherein said displaying information step displays information related to said color Doppler parameters in said study data set.

48. The method of claim 47 further comprising the step of providing velocity direction angles for information related to said motion data at points along the line of study in response to velocity direction angle information.

49. A display method for use in an ultrasound system comprising the steps of:

defining a line of study on a two-dimensional ultrasound image;

comparing information related to said ultrasound image along said line of study to reference data;

deriving at least one parameter from said comparison; and displaying information selected from the group of: information related to said ultrasound image for at least three points on said line of study, and said at least one parameter.

50. The method of claim 49 wherein said ultrasound image comprises motion data, and wherein said comparing step comprises comparing information related to said motion data to reference motion data to derive said at least one parameter.

51. The method of claim 50 wherein said ultrasound image comprises a color Doppler image, and wherein said comparison step comprises comparing information related to at least one color Doppler parameter of said motion data to at least one reference color Doppler parameter to derive said at least one parameter.

52. The method of claim 51 further comprising the step of providing velocity direction angles for said information related to at least one color Doppler parameter of said motion data at points along the line of study in response to velocity direction angle information.

53. The method of claim 51 wherein said color Doppler image comprises a color Doppler image of a patient and wherein said comparing step comprises comparing information related to at least one color Doppler parameter of said motion data to at least one reference color Doppler parameter related to a color Doppler image of said patient taken at an earlier time.

54. The method of claim 51 wherein said color Doppler image comprises a color Doppler image of a patient and wherein said comparing step comprises comparing information related to at least one color Doppler parameter of said motion data to at least one reference color Doppler parameter related to a color Doppler image of at least one other patient with normal or diseased conditions.

55. The method of claim 49 wherein said displaying step comprises displaying information related to said ultrasound image for at least three points on said line of study and displaying said at least one parameter.

56. The method of claim 49 wherein said displaying step comprises displaying information related to said ultrasound image for at least three points on said line of study as a profile curve.

57. The method of claim 49 wherein said displaying step comprises displaying said at least one parameter at as data selected from the group of: a quantity and a profile curve.

58. The method of claim 49 wherein said defining step comprises placing measuring icons at any two or more desired positions on said ultrasound image and selecting said line of study based on the positions of the icons.

59. The method of claim 49 wherein said displaying step comprises displaying information related to said ultrasound image for at least three points on said line of study as a set of estimated spectra along said line of study.

60. The method of claim 49 further comprising:

placing an icon at a position along the line of study; and displaying a spectral strip for said position with said display of information.

61. An ultrasound system for displaying line of study information comprising:

a display containing a two-dimensional ultrasound image:

a line of study on said two-dimensional ultrasound image;

means for generating comparison data as a function of information related to said line of study and reference data; and wherein said display further contains information selected from the group of: information related to said ultrasound image for at least three points along the line of study and said comparison data.

62. The system of claim 61 wherein said ultrasound image comprises a motion data image and wherein said means for generating comparison data comprises a means for generating data as a function of motion data related to said line of study and reference motion data.

63. The system of claim 62 wherein said ultrasound image comprises a color Doppler image, and wherein said means for generating comparison data comprises a means for generating data as a function of at least one color Doppler parameter of said motion data and at least one reference color Doppler parameter.

64. The system of claim 63 further comprising:

means for inputting velocity direction angle indication data; and means for determining velocity direction angles corresponding to said at least one color Doppler parameter of said motion data as a function of said velocity direction angle indication data.

65. The system of claim 63 wherein:

said color Doppler image comprises a color Doppler image of a patient; and said means for generating comparison data comprises means for generating data as a function of at least one color Doppler parameter of said motion data and at least one reference color Doppler parameter related to a color Doppler image of said patient taken at an earlier time.

66. The system of claim 63 wherein:

said color Doppler image comprises a color Doppler image of a patient; and said means for generating comparison data comprises means for generating data as a function of at least one color Doppler parameter of said motion data and at least one reference color Doppler parameter related to a color Doppler image of at least one other patient with normal or diseased conditions.

67. The system of claim 61 wherein said display comprises information related to said ultrasound image for at least three points along the line of study and said comparison data.

68. The system of claim 61 wherein said display comprises a profile curve.

69. The system of claim 61 wherein said means for generating comparison data comprises a means for generating data from the group of: a quantity and a profile curve.

70. The system of claim 61 wherein said line of study comprises at least two measuring icons at a first and second position, respectively, on said ultrasound image and at least one line connecting said at least two measuring icons.

71. The system of claim 61 wherein said display comprises a set of estimated spectra related to said ultrasound image for at least three points along the line of study.

72. The system of claim 61 further comprising:

an icon at a position along the line of study; and wherein said display further comprises a spectral strip for said position.

* * * * *

UNITED STATES PATENT AND TRADEMARK OFFICE

CERTIFICATE OF CORRECTION

PATENT NO. : 5,785,655

DATED : July 28, 1998

INVENTOR(S) : Goodsell, Jr. et al.

It is certified that error appears in the above-indentified patent and that said Letters Patent is hereby corrected as shown below:

In claim 40, line 5, after "comprises" insert --a means for displaying--.

Signed and Sealed this

Eighth Day of February, 2000

Attest:

Q. TODD DICKINSON

Attesting Officer

*Commissioner of Patents and Trademarks*